United States Patent [19]
Russell

[11] Patent Number: 5,146,288
[45] Date of Patent: Sep. 8, 1992

[54] PEARL LOUPE

[76] Inventor: Kenneth M. Russell, 4512 Avamere St., Bethesda, Md. 20814

[21] Appl. No.: 717,663

[22] Filed: Jun. 19, 1991

[51] Int. Cl.⁵ ............................................. G01N 21/87
[52] U.S. Cl. ............................................................ 356/30
[58] Field of Search ........................................... 356/30

[56]         References Cited
         U.S. PATENT DOCUMENTS 4,906,083  3/1990  Sattler .................... 356/30

FOREIGN PATENT DOCUMENTS

681/26    of 1926  Australia ........................... 356/30
421449   11/1925  Fed. Rep. of Germany ........ 356/30
458813    4/1928  Fed. Rep. of Germany ........ 356/30
592529    8/1925  France ................................. 356/30
606373    6/1926  France ................................. 356/30
183674    8/1922  United Kingdom .................. 356/30
253373    6/1926  United Kingdom .................. 356/30

*Primary Examiner*—F. L. Evans
*Attorney, Agent, or Firm*—Staas & Halsey

[57]         ABSTRACT

The invention relates to an apparatus for distinguishing cultured pearls from natural pearls by piercing the unidentified pearls with beams of light, preferably polarized, to reveal gross structural differences. The apparatus uses a light source, a polarizing filter, opaque shields, micro ports for light limitations, field magnifying lenses preferably 10× or 12×, and slides and other positioners to hold pearls singly or in strings.

8 Claims, 5 Drawing Sheets

PEARL LOUPE

BACKGROUND OF THE INVENTION

1. Field of the Invention

The invention is mainly directed toward enabling all persons but especially pearl dealers jewelers and gemologists to surely identify natural pearls and distinguish them from cultured pearls of lesser value. The jewelry industry's standard manual for identifications declares this uncertainty about pearls to be the most difficult distinction, even for gem experts and for lack of any alternative, requiring X-ray examination by special laboratories. Such reference may be inconvenient or impossible in many business situations.

The invention thus arrives against a background of widespread general confusion even among experts, that has endured all of the approximately 100 years since advent of cultured pearls looking somewhat like those natural ones treasured throughout the world for millennia. The Bible mentions pearls ten times, diamonds only three. The United States has imported in a year as much as 500 million dollars worth of cultured pearls and cultured pearl jewelry. Most such pearls may consist more than 90 percent of mother-of-pearl bead nucleus made from Mississippi or Tennessee river clamshell costing about 30 cents per pound.

The clamshell beads were found to be compatible material which when surgically inserted into the oyster, caused fewer mortalities of the host mollusks. In three years the added layers of nacre (calcium carbonate) add at most one-half millimeter of overcoat, equal to half the thickness of a paper match stick. Many cultured pearls have even less nacre. With the invention, the mostly straight lines of the bead inside become sharply visible, looking like the edge of a sandwich or a layer cake, a firm answer to identity. Most jewelers are aware in a general way of the cultured pearls pretense but find it profitable. Few of today's American customers have any acquaintance with real pearls. Most have never owned any.

Chiefly from estates there are still in private hands many real pearls, singly or in necklaces and these may confront the trader with decisions between a few hundred dollars and thousands. He may know his diamonds and rubies but be blind in pearls or be aware his expertise is limited.

2. Description of the Prior Art

In the past there have been many efforts and devices to separate natural and cultured pearls at a laboratory level. None was practical, convenient and certain.

One required a hole be drilled through the pearl. Then a tiny mirror and light were inserted and there might be seen the circular lines of added nacre. Another method was to measure the specific gravity against the known number for natural pearl, etc. It is sometimes suggested that a way to identify cultured pearls in a necklace is to hold the necklace in a straight line on white paper beneath a lamp then rotate the pearls to observe whether they show a flash when the covered mother-of-pearl beads reach an aspect reflecting light. Flashing would be from the bright plane of mother-of-pearl occurring twice in 360 degrees. Inasmuch as the beads are drilled at random, such coincidence is chancy. This technique offers nothing to verify natural pearls. All these and other attempts fell short of anything for widespread use.

The most effective method and still the general last resort, has been X-ray and that only in a few special laboratories, not your neighborhood dentist. X-ray has offered views of many natural pearl's internal structures and may also reveal diagnostic fluorescence.

Candling viewing pearls of any kind by placing a light behind them, has been mentioned repeatedly but always with disdain. Candling or backlighting to see the interior, has long been familiar for the detection of hens eggs with an embryo, to cull these from food marketing. But until the invention, no pearl-identifying apparatus has used transmitted light and been practical and dependable. There are patents for identification and evaluations of gemstones. These variously rely upon the degrees of bending light, computer digitalizing of colors, etc. and all relate to mineral gems, not organics such as pearls. The pearl is the only gem that neither needs nor will tolerate without harm embellishment by man. This doubtless has postponed its technical conquest.

SUMMARY OF THE INVENTION

The invention represents a new approach to apparatus equipped and designed specifically to evidence the differences between natural pearls and cultured simulations. No previous apparatus of which the inventor is aware has ever successfully used candling technique now coupled for the first time with a convenient dark chamber and with versatile holding arrangements. These combine to reveal pearl differences such as the layer edge lines in clamshell bead cultured, the yellowish amorphous cores of tissue nucleated cultured and the uninterrupted interior of real pearls. But the invention's efficient joining of the dark chamber and a small beam of light-preferably polarized, to pierce the pearl upward toward the user has brought a new and exciting advantage based on utilizing a hitherto unknown and phenomenal property of natural pearl and no other. This is the apparatus' stimulation of luminescence created evenly throughout the pearl under examination. The natural pearl glows. No other does. Although other structural findings shown by the invention will be supportive, the inventor estimates that this new evidence may prove to be the single most dependable and primary proof of natural pearl, apart from the mentioned complicated X-ray study in laboratories.

It is a primary objective of this invention to provide all apparatus to determine positively the observable differences between natural (real) pearls and cultured simulations thereof.

It is another object of the invention to use a small beam of intense light, preferably polarized admitted into a darkened viewing chamber, to reveal such differences.

It is another object to provide said viewing chamber with holding facilities to pose precisely pearl objects of various sizes and shapes, singly or strung in jewelry, for examination and indentification.

Another object is to create a situation of maximum contrast between light and darkness that will be adequate for natural pearl to demonstrate its property of glowing spectacularly.

A further objective is to provide a sharp view of the internal straight lines and light and dark lateral zones that identify pearls made on a bead composed of clamshell, as are most cultured pearls.

Yet another objective is to provide a clear view of the amorphous internal core, usually a yellow orange color that identifies a cultured pearl built around a bit of mollusk tissue as nucleus.

Yet another objective is to make apparent any imitation pearls made with a solid, wax filled, or hollow glass bead. The apparatus makes each of these distinct.

DRAWINGS

FIG. 1 shows an overall view of the construction of the apparatus.

FIGS. 2A and 2B respectively show schematic views of the construction of natural and most cultured pearls. More specifically, FIG. 2A shows a cross section of a round natural pearl, while FIG. 2B shows a cross section of a cultured pearl having a bead nucleus made from clamshell which is layered mother-of-pearl.

FIGS. 3A and 3B respectively show a front side view and a left side view of the apparatus of FIG. 1.

Figure 6A:
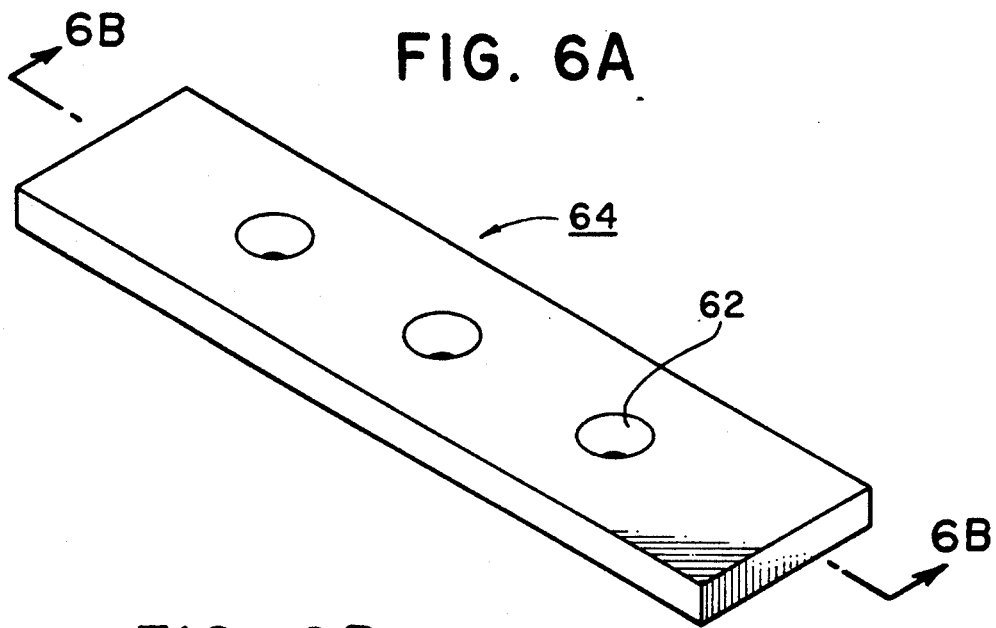
Figure 6B:
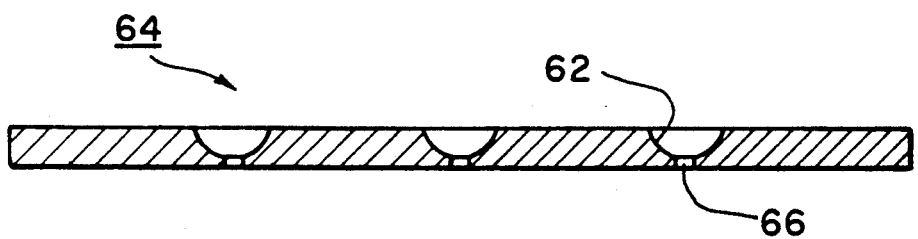
Figure 6C:
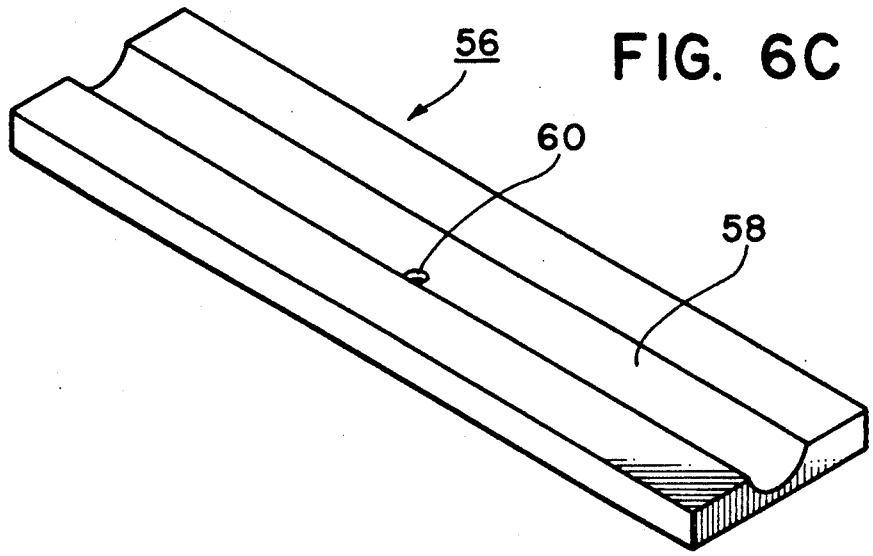

FIGS. 6A and 6B respectively show an overall view and a cutaway side view of a first slide tray that may be used as a holder. FIG. 6C shows an overall view of a second slide tray that may be used as a holder.

DESCRIPTION OF THE PREFERRED EMBODIMENT

At the outset it is important to note that the major features of the preferred embodiment are constructed or arranged to exploit the differences in the appearance of natural and cultured pearls when illuminated.

Natural pearl is shown by this invention to have a basic structure which in darkness accepts an intense light beam striking only a small area of its surface and then, redistributes said light to suffuse the entire body and make it glow markedly. Neither cultured nor imitation pearl does this. Only the elements of this invention reveal this phenomenon. By far the largest proportion of cultured pearls for many years have been made and presently are made, as shown in FIG. 2B, by deceiving the molluscs into adding nacre layers 26 made, to an implanted bead 22 shaped from clam shell material. The invention reveals laminations of such beads as quite straight lines 24 or zones 28. Natural pearls have no such lines or zones.

Figure 2A:
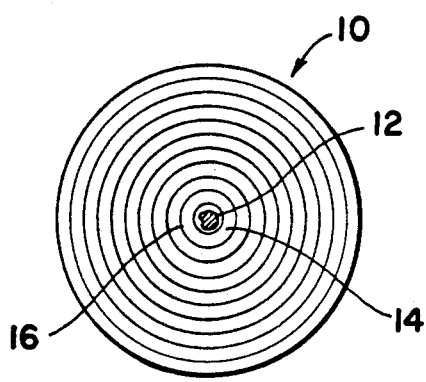
Figure 2B:
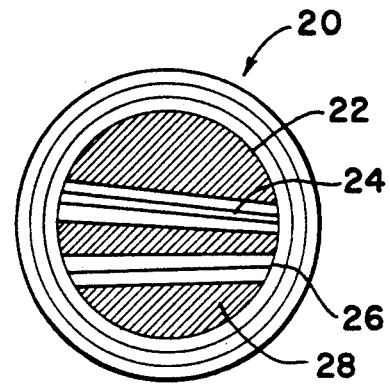

The great disparity between, the make-up of the two kinds of pearls is generally shown in FIGS. 2A and 2B. FIG. 2A shows a cross section of a round natural pearl 10. The natural pearl 10 consists entirely, other than the core irritant 12, of successive overlays 14 of micro platelets of aragonite (calcium carbonate) that have crystallized from nacre and arranged themselves without exception at 90 degrees to an imaginary line from the pearl's 10 center. The layer lines 16 of overlays 14 are not normally visible because each layer totally envelops the natural pearl 10, leaving no edges. Light striking these platelets at any substantial angle is readily transmitted via a narrowing cone to the pearl's 10 center. Said light then is shunted in all directions excepting the source cone. Hence the glow previously described.

FIG. 2B shows a cross section of a cultured pearl 20 having a bead nucleus 22 made from clamshell which is mother-of-pearl having layer lines 24. The situation of cultured pearl 20 shown in FIG. 2B depicts the edge blunting of any such incoming light plus the dampening effect of much conchiolin. Without light absorption, much of any imposed light goes instead into reflectance which may account for the shininess of all cultured pearls compared to the "soft" luster of naturals.

Figure 5:
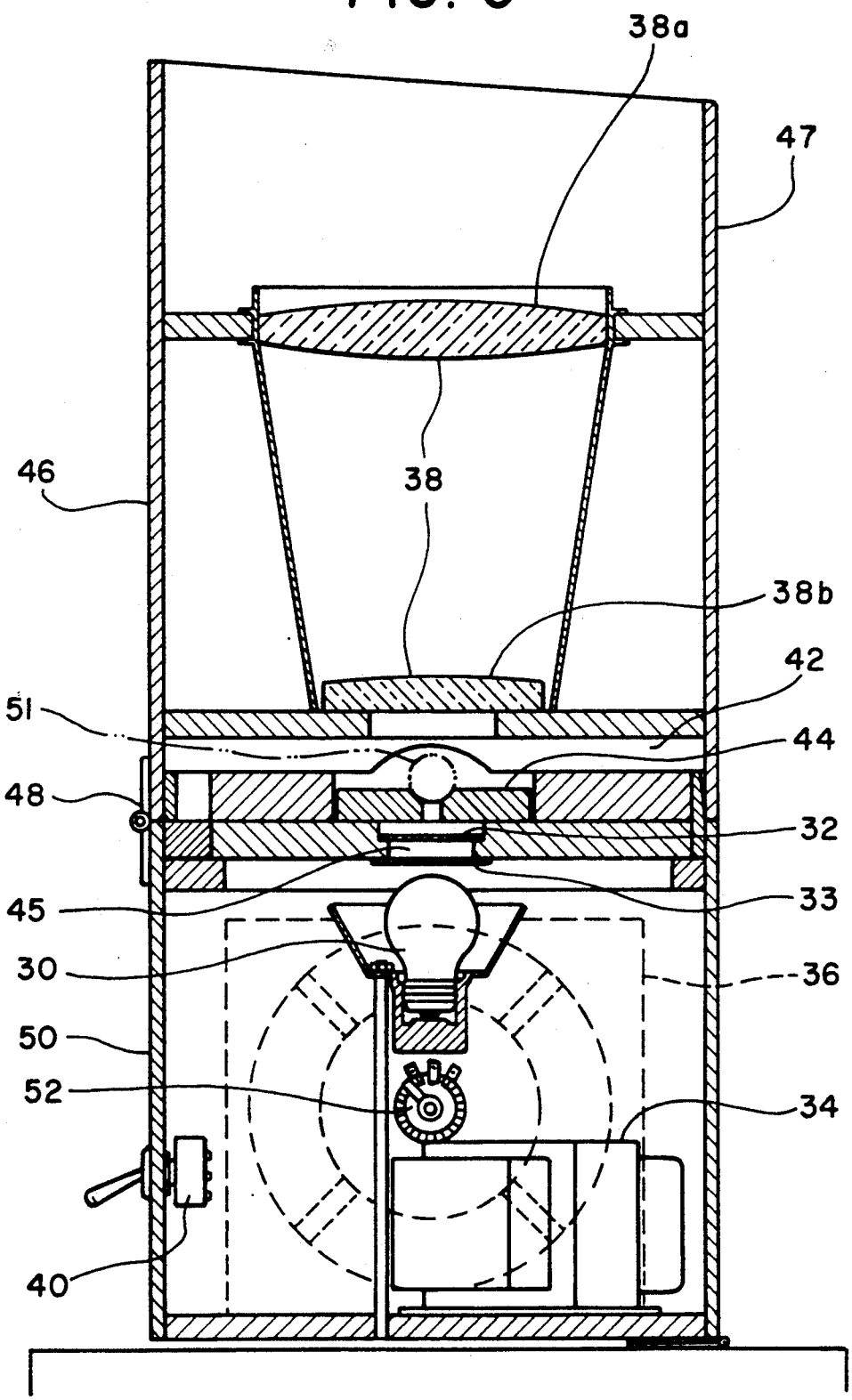
FIG. 5 shows a cutaway right side view of the apparatus of FIG. 1.

The apparatus of the invention, as best seen from FIG. 5, comprises an intense light source 30 of about 12 watts (e.g., 12 V, 12 W, GE 93 bulb) with infinite control, preferably with a polarizing filter 32 and light diffuser 33, also a stepdown transformer 34(e.g., 1.2 A, 6.3-0-6.3 V), a cooling fan 36 (e.g., 12 V, 0.12 A, brushless fan), direct magnifying lens system 38 having magnifying lenses 38a, 38b with about 10× or 12× total power, an on-off switch 40, an 115 A.C. voltage intake (not shown), an effective dark chamber 42, and pearl holder 44. It comprises two separable boxes, an upper box 46 hinged by an upper hinge 48 or placed atop a lower box 50 for functional purposes. The lower box 50 has a light opening 45. The upper box 46 has a hood extension 47 to reduce extraneous light and contains the direct magnifying lens system 38, preferably of 10× or 12× power. The lower box 50 contains the lighting system to illuminate pearls 51 placed near the top of lever box 50. Any sort of intense lighting system would do. It should have a dimmer switch 52(e.g., 15Ω, rheostat) to minimize any eyestrain on the user if maximum power is not needed.

Preferably the light source 30 would be an incandescent bulb of about 12 watts powered indirectly from a usual 115 volt AC outlet, for convenience. The direct power supply could be from a stepdown transformer 34 in the lower box 50, producing say 12 volts. An off-on power switch 40 and a cooling fan 36, should be included.

Figure 3B:
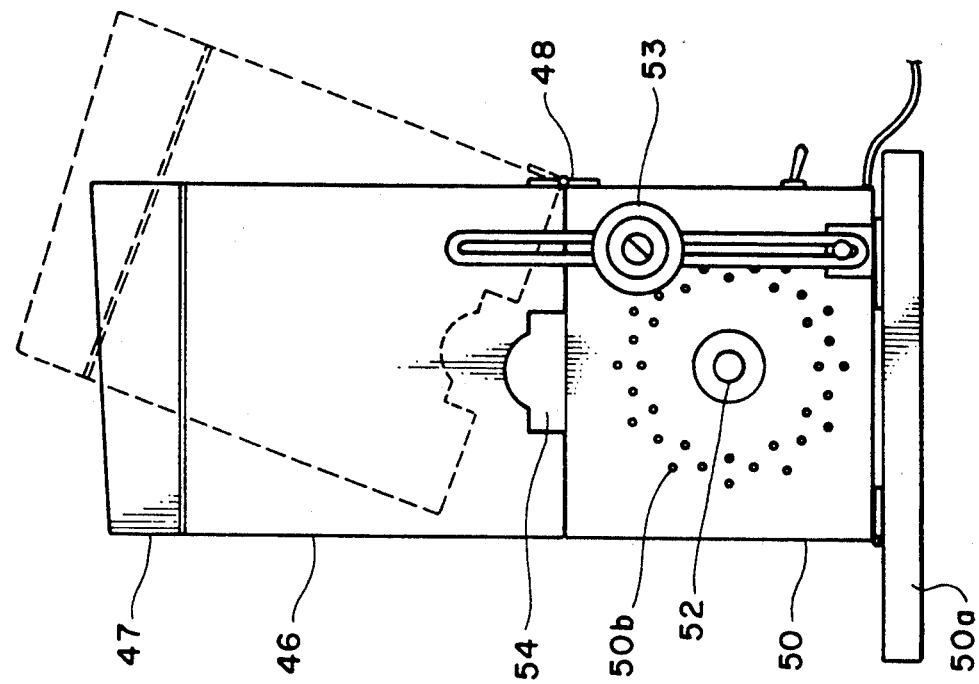
Figure 3A:
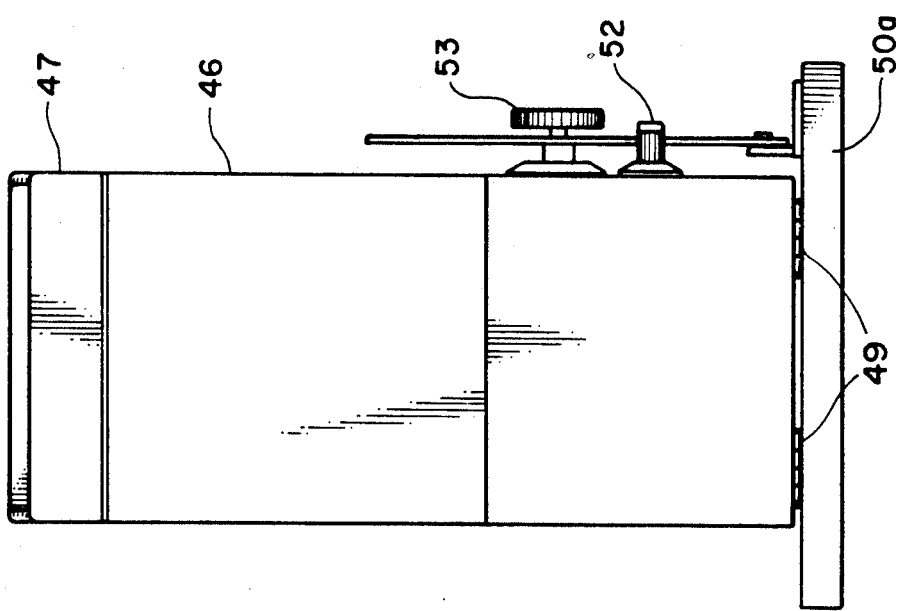

As best seen in FIGS. 3A and 3B, lower box 50 may be attached to a base 50a by forward tilt hinges 49, and the angle of lower box 50 relative to base 50a may be adjusted by forward tilt adjuster 53. Lower box 50 also includes air exhaust vent 50b.

Figure 1:
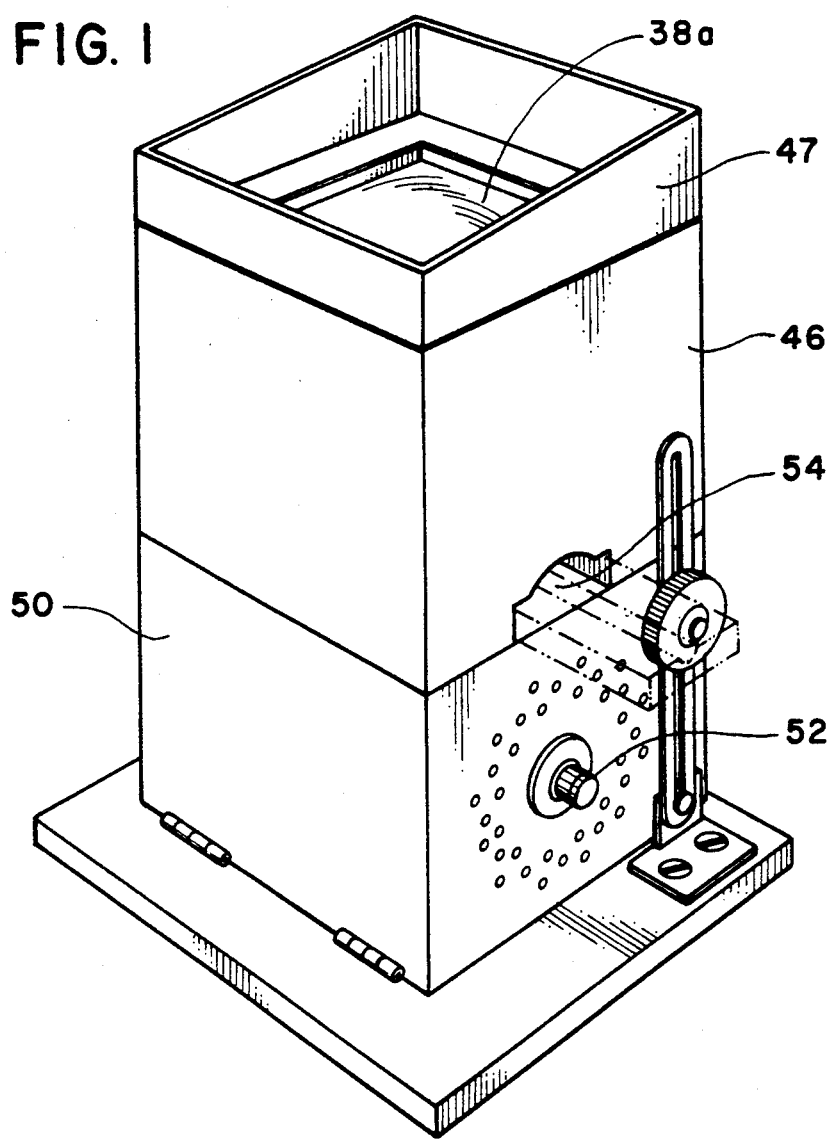
Figure 4B:
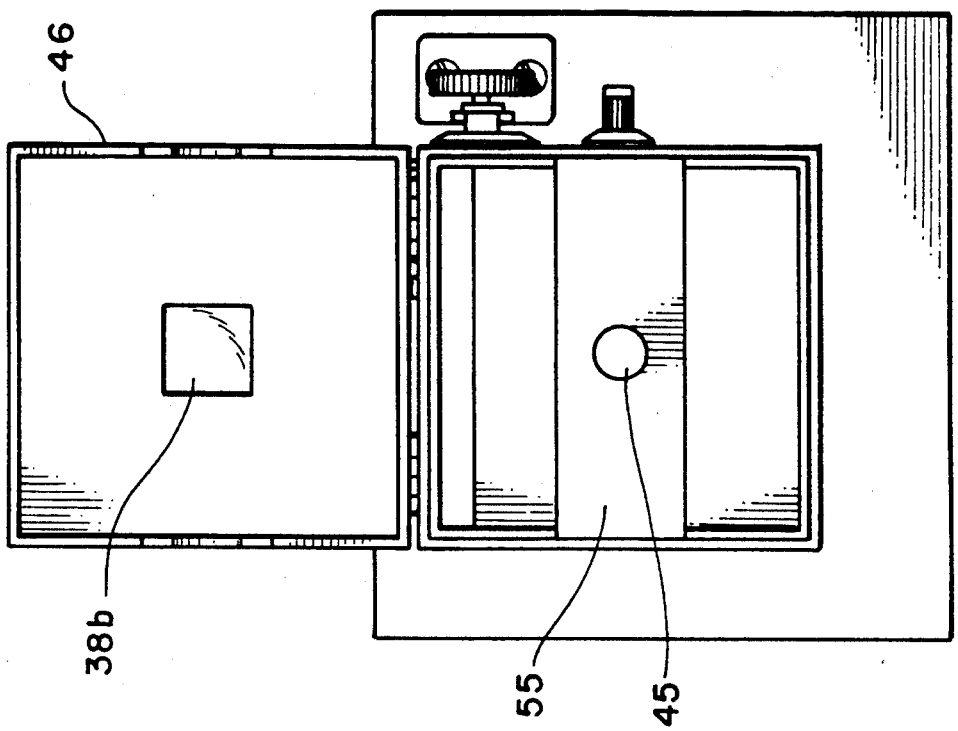
FIGS. 4A and 4B show top views of the apparatus of FIG. 1 with its top closed and opened, respectively.
Figure 4A:
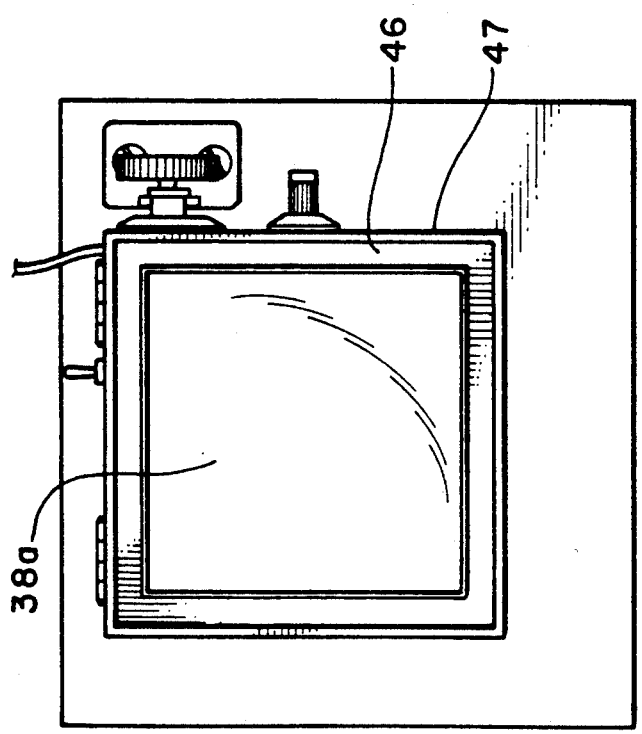

A pearl holder 44 to position pearls 51 in line with the light beam and vision arrangement is placed near the top of the lower box 50 and may rest upon it. Pearl holder 44 is accessible by lifting the upper box 48. Or, as shown in FIG. 1, the viewing site may be accessed by sliding special slabs (shown in phantom line) of opaque plastic or other material, carrying target pearls, through slots 54 that may be cut into the lower edge of the sides of said upper box 46. As best shown in FIG. 4B, the slabs slide through a slide channel 55 provided on the upper portion of lower box 50. Slide channel 55 may have a width of 38 mm, for example. Light opening 45 is disposed at the bottom of slide channel 55, and may have a width of 17 mm, for example. Said slabs or slides may be of various design. For example, as shown in FIG. 6C, a slide 56 may be grooved from end to end to compose a rounded trough 58 for a string of pearls to rest with small apertures 60 drilled vertically at several points through the bottom of the trough to admit a beam of light. Or, as shown in FIGS. 6A and 6B, there may be rounded craters spaced at intervals along the center line of a slide 64 with a port 66 cut through the base of each of said craters 62 to admit the beam. Other configurations are possible so long as they achieve the basic purpose of fixing the target pearl over the intensive light and directly below the users line of sight.

The apertures 60 and parts 66 for the light should not be large, preferably not more than 1/16 to ⅛ inch (1.6 mm-3.2 mm). Of course any lighting apparatus that can also hold a pearl between the light beam and the viewing lens can work in some degree. But it is the strong polarized beam combined with virtually complete darkness that sets the stage for the natural pearl to dramatically declare itself by the glowing effect absent in cultured or imitation pearls.

The polarized filter 32 does two things. It narrows the applied beam to eliminate scattered light that would mar the darkness, and it makes the magnified images sharper. It is helpful but perhaps not entirely essential.

I claim:

1. An apparatus for determining whether a pearl is natural, comprising:

a light source;

eyepiece means for magnifying and for receiving light from said light source;

pearl support means for holding a pearl under observation between said light source and said eyepiece means; and housing means, encompassing said light source and said pearl support means, for creating a substantially darkened viewing chamber and for eliminating extraneous light from entering said substantially darkened viewing chamber, said pearl support means having a relatively small aperture positioned so as to allow light from said light source to illuminate said pearl, whereby luminescence throughout said pearl is stimulated only when said pearl is natural.

2. The apparatus of claim 1 having a polarization filter capable of polarizing light, said polarization filter located between said light source and said pearl support means.

3. The apparatus of claim 2 wherein said aperture is about 1.6-3.2 millimeters in diameter.

4. The apparatus of claim 3 where said housing means has left, right, front and back walls and has slots placed in two of said walls, said walls with said slots being opposite each other, said pearl support means made of opaque material and capable of being held in said slots, said pearl support means having a notch capable of holding pearls of various sizes, said notch being of half round shape and said aperture being in connection with the bottom of said half round shape.

5. The apparatus of claim 1, wherein said housing means includes:

a first portion encompassing said light source and having means for removably receiving said pearl support means; and a second portion encompassing said eyepiece means.

6. The apparatus of claim 5, wherein said first portion and said second portion of said housing means are movably secured to one another by a hinge.

7. A method for determining whether a pearl is natural, comprising:

placing a pearl in a relatively darkened viewing chamber and eliminating extraneous light from entering said relatively darkened viewing chamber; and placing a light source emitting a relatively small beam of light so as to illuminate a small portion of a side of the pearl that is facing said light source, whereby luminescence is stimulated throughout said pearl only when said pearl is natural.

8. An apparatus for determining whether or not a pearl is natural, comprising:

a light source;

a substantially dark viewing chamber arranged so as to eliminate extraneous light from entering said substantially dark viewing chamber and having a pearl support means for holding a pearl in said substantially dark viewing chamber, said pearl support means having an aperture optically connected to said light source and positioned so as to direct a beam of light from said light source onto a surface of said pearl in a substantially radial direction of said pearl such that luminescence is stimulated in said pearl only when said pearl is natural; and lens means, connected to said substantially dark viewing chamber, for magnifying and viewing said pearl.

* * * * *